United States Patent [19]

Pedroso et al.

[11] Patent Number: 4,516,437
[45] Date of Patent: May 14, 1985

[54] MICROSAMPLE HANDLING APPARATUS

[75] Inventors: Raul I. Pedroso, Miami; Robert S. Coulter, Hialeah, both of Fla.

[73] Assignee: Coulter Corporation, Hialeah, Fla.

[21] Appl. No.: 478,134

[22] Filed: Mar. 23, 1983

[51] Int. Cl.³ ............................................. G01N 35/06
[52] U.S. Cl. ..................................... 73/864.22; 134/21
[58] Field of Search ......................... 73/864.22; 134/21

[56] References Cited

U.S. PATENT DOCUMENTS

| 3,266,322 | 8/1966 | Negersmith | 73/864.22 |
| 3,719,086 | 3/1973 | Bannister et al. | 73/864.22 |
| 3,911,749 | 10/1975 | Hendry | 73/864.22 |
| 4,064,886 | 12/1977 | Heckele . | |
| 4,166,305 | 9/1979 | Gustafsson . | |
| 4,217,780 | 8/1980 | O'Connell et al. . | |
| 4,311,484 | 1/1982 | Fosslien . | |

Primary Examiner—S. Clement Swisher

Attorney, Agent, or Firm—Stephen A. Roen; Gerald R. Hibnick

[57] ABSTRACT

Method of and apparatus for handling a microsample comprising a probe for aspirating a sample and a cleaning mechanism having a passageway within which the probe is movable. The passageway has a cleaning chamber having opposite ends, one end being open to the atmosphere and proximate the sample. The cleaning mechanism further includes a fluid directing means and two vacuum applying means, the vacuum applying means being disposed at opposite ends of the chamber and the fluid directing means being disposed between them. During a cleaning mode the fluid directing means directs a wash fluid against the probe and the vacuum applying means removes the wash fluid, prevents exiting of the wash fluid and drys the probe, the later two by permitting gas from the atmosphere to flow into the cleaning chamber.

20 Claims, 6 Drawing Figures

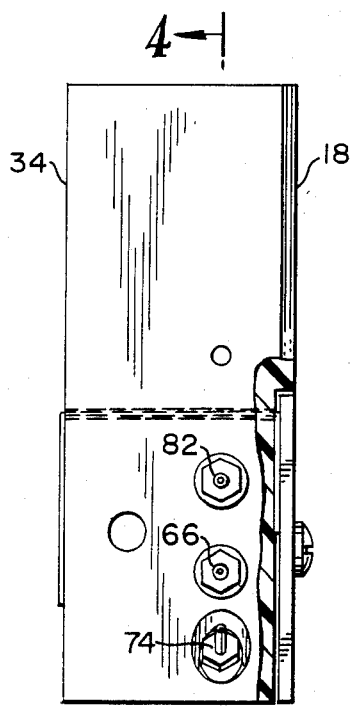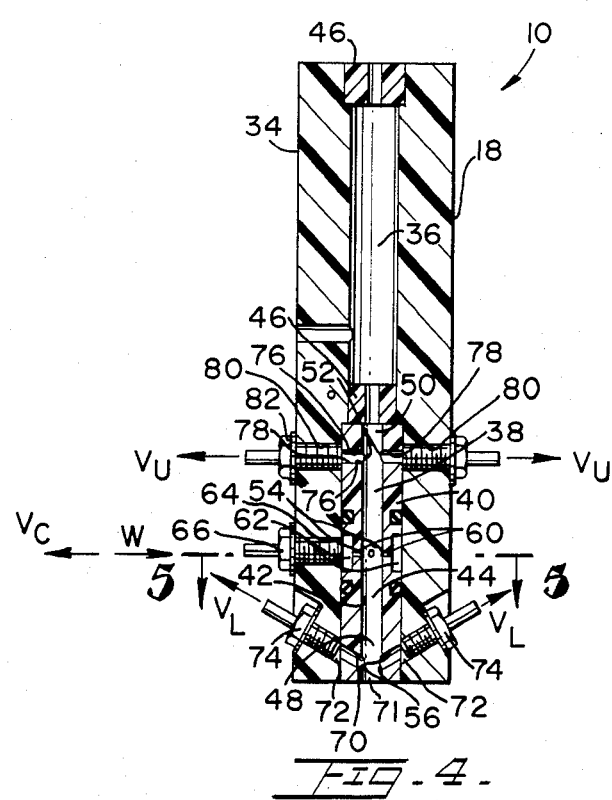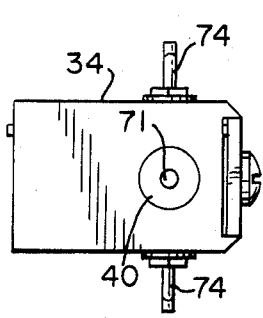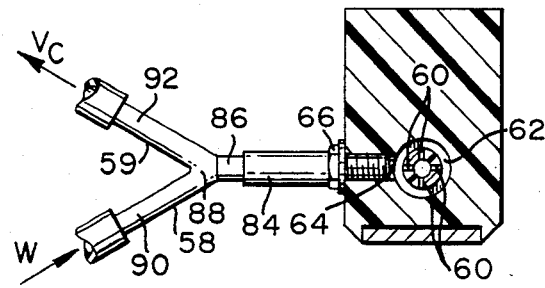

MICROSAMPLE HANDLING APPARATUS

BACKGROUND OF THE INVENTION

The invention relates to an apparatus and method for cleaning a probe between fluid sampling operations of the probe. More particularly, this invention concerns the external washing and drying of a probe preparatory to its use with another sample.

In sample analysis and cell sorting systems it is necessary to virtually eliminate sample contamination, while rapidly and repetitively sampling successive samples, particularly where a large number of different samples are to be processed automatically. Preferably, the apparatus should be as simple and compact as possible, as well as perform both sampling and cleaning in situ, that is in the same lateral position. Some large size sample analysis and cell sorting systems such as the DACOS ™ Chemistry System, manufactured by Coulter Electronics, Inc., Hialeah, Fla., utilize transfer mechanisms to laterally move an axially movable, vertically oriented, sampling probe between sampling operations for cleaning to a closed bottom cleaning station. Systems that utilize an axially movable but horizontally oriented sample probe and an opened ended cleaning station, such as disclosed in U.S. Pat. No. 4,311,484, issued Jan. 19, 1982, require closed sample containers and relatively elaborate sample feeding mechanisms. Systems that do utilize an axiable movable, vertically oriented, sampling probe which do not require such transfer mechanisms and instead utilize separate movable washing-drying mechanisms and waste units, such as disclosed in U.S. Pat. No. 4,217,780, issued Aug. 19, 1980, are relatively complex in design. Furthermore, none of such systems utilizing an opened ended cleaning station is ideally suited for automatically processing a large number of samples individually contained in the separate, open, wells of a standard twenty-four or ninety-six well microculture plate such as a MICROTITER ® plate. (MICROTITER is a registered trademark of Dynatech Laboratories, Inc.)

SUMMARY OF THE INVENTION

It is, therefore, an object of this invention to provide an improved microsample handling apparatus and method for cleaning its sampling probe.

Another object of the invention is to provide an improved microsample handling apparatus and method for externally cleaning, washing and drying, its sample probe.

A further object of the invention is to provide improved microsample handling apparatus and method for cleaning its sample probe whereby sample contamination is virtually eliminated.

A still further object of the invention is to provide a simple and compact microsample handling apparatus and method for cleaning its sample probe.

Still another object of the invention is to provide an improved microsample handling apparatus and method for cleaning its sample probe without the necessity of any lateral movement between the probe and its cleaning station.

Another object of the invention is to provide an improved microsample handling apparatus and method for cleaning a sample probe wherein said apparatus remains laterally fixed in place when the cleaning is performed after sampling.

A further object of the invention is to provide a simple and compact microsample handling apparatus and method for cleaning a sample probe wherein said apparatus remains laterally fixed in place when said cleaning is performed after sampling.

A still further object of the invention is to provide an open ended microsampling handling apparatus and method for cleaning a sample probe which does not require an elaborate sample feeding mechanism.

Another object of the invention is to provide an open ended microsampling handling apparatus and method for cleaning a sample probe which is ideally suited for automatically processing a large number of open samples.

The foregoing and related objects are obtained in accordance with the invention which, in its broader aspects, provides a microsample handling apparatus and method for cleaning a fluid probe means having a probe tip. The apparatus comprises the probe means for aspirating a sample and a cleaning mechanism having a passageway within which the probe means is movable. The passageway has a cleaning chamber having opposite ends, one end being open to the atmosphere and proximate to the sample. The cleaning mechanism further includes a fluid directing means and two vacuum applying means, said vacuum applying means disposed at opposite ends of said chamber and said fluid directing means disposed between them. The fluid directing means directs a wash fluid against said probe means during a cleaning mode and said vacuum applying means removes the wash fluid, prevents exiting of the wash fluid and drys the probe means, the later two by permitting gas from the atmosphere to flow into said cleaning chamber. The method of cleaning the probe means within the cleaning chamber of the cleaning mechanism, said cleaning chamber which has a first open end and a second end, and a plurality of cleaning ports, comprises the step of: moving the probe means to be cleaned within said cleaning chamber and externally: directing a flow of washing fluid against said probe means, drawing said flow of washing fluid past said probe means, and drawing a flow of gas from the atmosphere past said probe tip when it is within said cleaning chamber.

BRIEF DESCRIPTION OF THE DRAWINGS

The invention is illustrated in the drawings of which:

FIG. 2 is a side elevation view, partly in section, of the microsample handling apparatus shown in FIG. 1, but without its probe;

FIG. 3 is a bottom elevation view of the embodiment of FIG. 2;

FIG. 4 is a vertical section on line 4—4 of FIG. 2;

FIG. 5 is a horizontal section on line 5—5 of FIG. 4 and a Y-connector assembly coupled to its fitting.

DETAILED DESCRIPTION OF THE INVENTION

Figure 1:
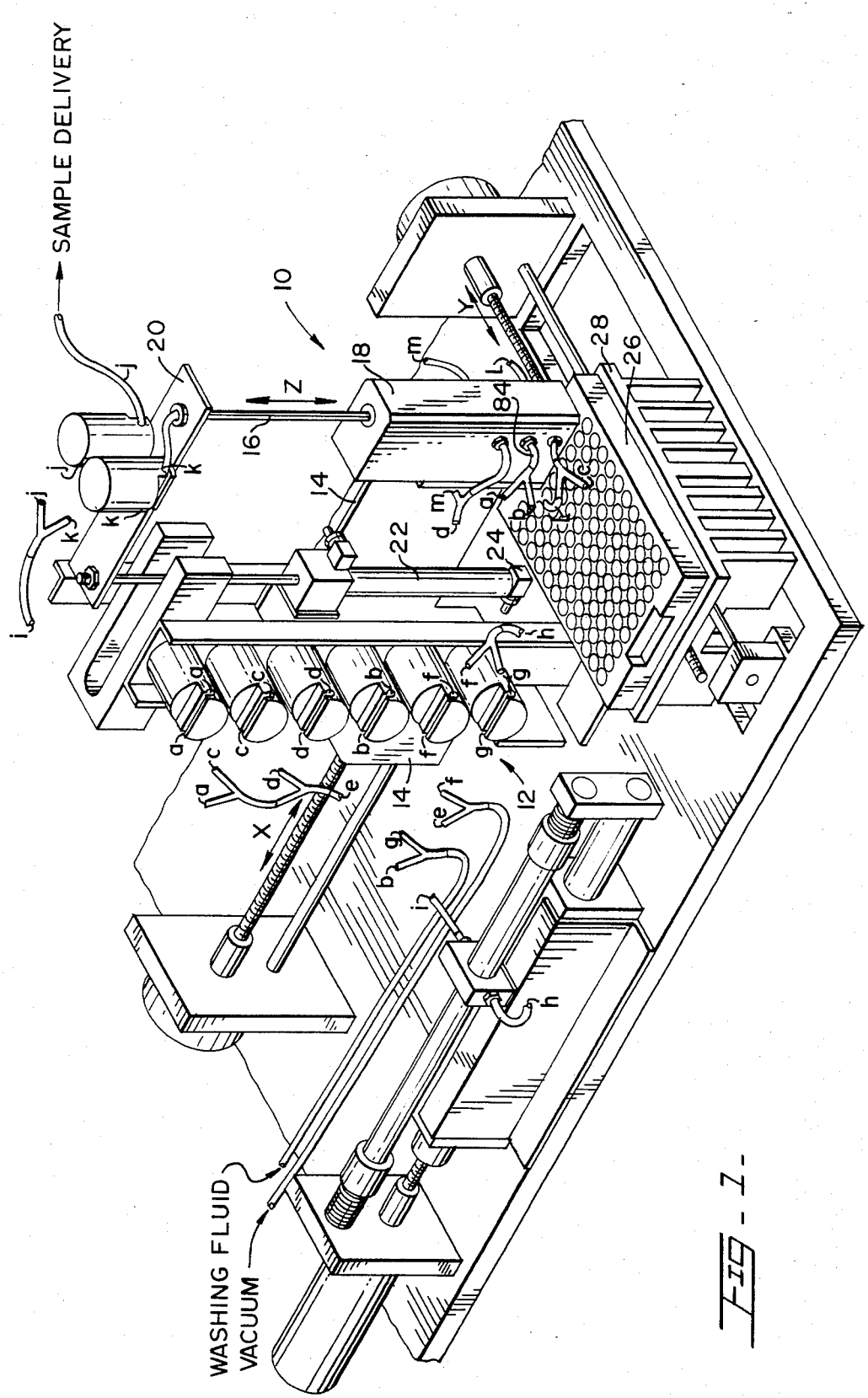
FIG. 1 is a perceptive view of the microsample handling apparatus of the invention and a partial view of a microsample handling system of which it is a part with its tubing and connections fragmentally shown.
Figure 6:
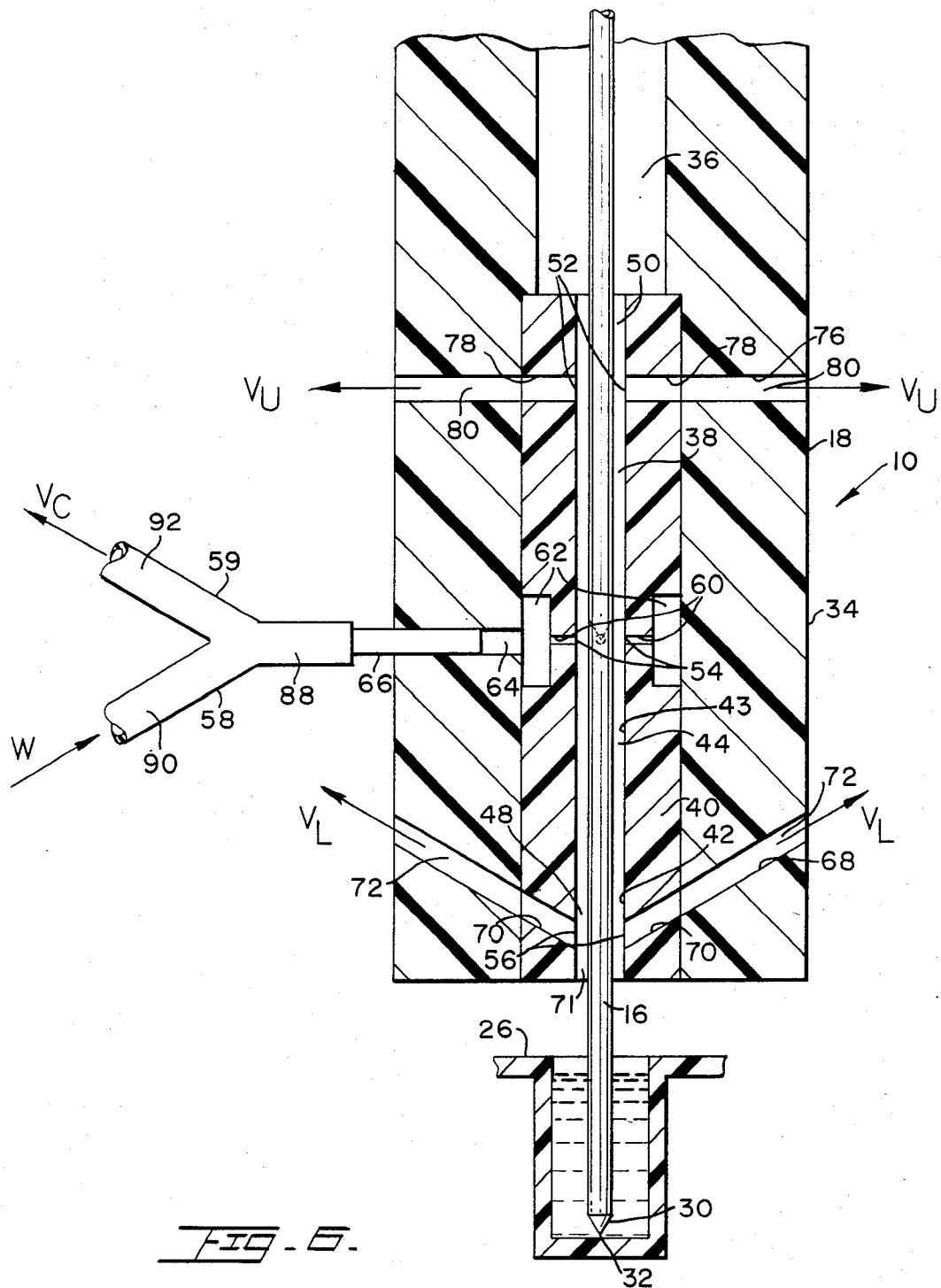
FIG. 6 is an enlarged, simplified, view of FIG. 4 with the probe being shown in its sampling position and, in a phantom view, in its retracted position.

Referring now to the drawings, particularly to FIG. 1, a microsample handling apparatus 10 is constructed in accordance with a preferred embodiment of the invention which is part of a microsample handling system 12 (partially shown). The microsample handling system 12 operates with cell analyzing and sorting systems for biomedical investigation, such as a COULTER® EPICS®V System, described in its product reference manual of February 1982, part number 4235066B, available from Coulter Electronics, Inc., Hialeah, Fla., and is incorporated herein, by reference, and can replace the viable sample handling system subcomponent thereof as the source of the sample into said EPICS®V System. (COULTER is the registered trademark No. 995,825 of Coulter Electronics, Inc., Hialeah, Fla., and EPICS is the registered trademark No. 1,175,973 of Coulter Corporation, Hialeah, Fla.)

The microsample handling system 12 comprises a carrier assembly 14, which is movable forwards and backwards, as shown by the arrows X, by conventional means such as stepper motors (not shown). The microsample handling apparatus 10 is fixedly mounted at the front portion of the carrier assembly 14, which apparatus includes a probe means, aspirator or probe 16. This probe 16 is both axially movable within and movable together with a cleaning mechanism or station 18, described in detail hereinafter. The upper end of the probe 16 is fixedly connected to a horizontal extension arm 20 seated on the top of the carrier assembly 14 and is axially movable by said arm 20 within the cleaning station 18.

The other end of the arm 20 is vertically movable by conventional pressure actuated means, including an air cylinder 22 which has an air fitting 24 connected to a conventional, controlled source of air pressure (not shown). In an automatic mode, samples are taken from a sequence of wells in a MICROTITER® plate or sample container 26, preferably with ninety-six wells, which plate 26 is laterally moved under the probe 16, forwards and backwards, as shown by arrows Y, on a holder 28 by conventional means, such as a stepper motor (not shown). In a manual mode, the microsample handling apparatus 10 is moved forward in the X direction to take a sample from a single sample or culture tube (not shown) held by an operator and properly positioned below the probe 16. Sampling and cleaning, in both the automatic and the manual mode, are performed while the microsample handling apparatus 10 remains laterally fixed in place, as explained in detail hereinafter.

Aspiration and delivery of sample into an EPICS®V System is conventionally accomplished as is the control of the cleaning of said probe 16, as described in detail hereinafter, through the use of appropriate pneumatics and hydraulics, including valves 29, all under the control of a microprocessor (not shown).

Referring now specifically to FIGS. 2–6, the microsample handling apparatus 10 comprises the probe means 16, which is axially disposed within the cleaning station 18, for aspirating a sample. Probe 16 includes a probe tip 30 and is of conventional single tube design, preferably of corrosion resistant steel, type 316 and of half hard temper, with an aspirating opening 32 at its end. Its exterior is preferably TEFLON® coated, 0.002±0.003 thick, in inches. (TEFLON is a registered trademark of Du Pont de Nemours, E. I., and Company.) The cleaning station or means 18 includes a rectangular shaped, elongated, carrier member 34 having an upper bore 36 axially extending through an upper portion of the carrier member 34 and communicating with a concentrically disposed lower bore 38 of slightly greater diameter, which axially extends through a lower portion of the carrier member 34. A generally cylindrical manifold 40, preferably formed of acrylic PLEXIGLASS® plastic material, is connected in sealing engagement in the lower bore 38 formed in carrier member 34 and includes, as a part of its interior wall, an internal passageway 42 having walls 43 which define or form a cleaning chamber 44. Disposed at the upper and lower ends of the upper bore 36 are bushings 46 to properly locate and guide probe 16 within the passageway 42 and within which it is axially movable. Cleaning chamber 44 has opposite ends, lower and upper ends, 48 and 50, respectively, and a plurality of cleaning ports formed in the internal passageway 42, including a pair of opposing upper cleaning ports 52, center cleaning ports 54, preferably four in number each of which is equally spaced around the central portion of the periphery of the passageway 42, and a pair of opposing lower cleaning ports 56. The lower or first end 48 of the cleaning chamber 44 is open to the atmosphere and is disposed proximate to the sample. The other end, upper or second end 50, is disposed distally from the sample. Communicating with the central portion of the cleaning chamber 44, through the center ports 54, are first and fourth means 58 and 59, respectively, including four center side passageways 60, each directed radially and inwardly toward the center axis of the internal passageway 42, and having their external ends opening into an annular chamber 62 formed in the exterior wall of the manifold 40, which in turn opens into a single center side bore 64, which has a fluid fitting 66 inserted therein. The lower portion of the cleaning chamber 44 communicates through said lower cleaning ports 56 with a second means 68, including, preferably, a pair of lower side passageways 70 disposed at the mouth 71 of the open-ended chamber 44. Each of the lower side passageways 70 is directed angularly, preferably sixty degrees from the axis of the chamber 44, and radially inwardly toward the center axis of the internal passageway 42, and having each of their external ends opening directly into a lower side bore 72, which has a fluid fitting 74 inserted therein. The upper portion of the cleaning chamber 44 communicates through the upper ports 52 with a third means 76, including, preferably, a pair of upper side passageways 78 disposed at the upper end 50 of said chamber 44, each of said upper side passageways 78 are directed radially and inwardly toward the center axis of the internal passageway 42 and having each of their external ends opening directly into a upper side bore 80, which has a fluid fitting 82 inserted therein.

The first and fourth means 58 and 59, respectively, further include, in common, a conduit means or line 84, preferably of clear plastic tubing, connected at one end to the fluid fitting 66 and at its other end to a branch portion 86 of a Y-connector 88. The first means 58 additionally includes a stem 90 of Y-connector 88 which is coupled to a washing fluid source shown diagrammatically by an arrow W. The fourth means 59 additionally includes a stem 92 of the Y-connector 88, which is coupled to a vacuum drain shown diagrammatically by an arrow $V_C$. The second means 68 further includes conduit means (not shown) connected at one end to both fluid fittings 74, has its other end to the vacuum drain and is shown diagrammatically by arrows $V_L$. Similarly the third means 76 further includes conduit means (not shown) connected at one end to both fluid fittings 82, and has its other end coupled to the vacuum drain and is shown diagrammatically by arrows $V_U$.

It will be understood that where the status of ports are specified as being either "close" or "open", or "closed" or "opened", or the like, such status refers to a source of a negative pressure (a vacuum), wash fluid, or a flow of air and/or liquid, or the like being either prevented or permitted to flow past or be gated through said ports through controlled valves, such as pinch valves, under the control of a controlling means, such as a microprocessor.

Referring again to FIGS. 2-6 in both the automatic and manual modes, when the probe 16 is instructed to descend from its retracted or up position into the sample container 26, that is when its probe tip 30 is in the center portion of the cleaning chamber 44 and when its tip end is aligned with the axial centers of said center ports 54, the lower ports 56 are opened to the vaccum $V_L$, and remain open until the probe 16 enters the sample container 26, the probe's down position, at which time each of the three series of cleaning ports, upper ports 52, center ports 54, and lower ports 56, are sequentially opened and closed in the aforesaid order, to air dry the probe 16 by drawing into the cleaning chamber 44, through its mouth, a flow of air or gas from the atmosphere through the opened ports, all prior to aspiration of the sample. After the sample is aspirated or drawn through the probe 16, while the probe 16 is in the down position, and until it is retracted into the up position, the first part of a cleaning cycle or mode is initiated to clean the outside of the probe 16 by first reopening lower ports 56 to the vacuum $V_C$ and then directing a flow of washing fluid W, such as ISOTON ® liquid, against the exterior of the probe 16 through opened center ports 54, while maintaining the lower ports 56 open. (ISOTON is the registered trademark No. 848,055 of Coulter Electronics, Inc., Hialeah, Fla.) During this period of time all the wash fluid W and any sample on the exterior of the probe 16 is drawn or discharged through opened lower ports 56 to waste. The probe 16 then is instructed to move to its up position, which initiates the second part of the cleaning mode, and, as it starts to move upwards, the flow of washing fluid W is continued for an appropriate period of time. When the probe 16 reaches its retracted position, the following sequence occurs: the upper ports 52 are open to the vacuum $V_U$, the lower ports 56 are closed, the center ports 54 are closed to the wash fluid while simultaneously these same center ports 54 are opened to the vacuum $V_C$, and then both the center and upper ports 54 and 52, respectively, are closed to their vacuums $V_C$ and $V_U$, respectively. Accordingly during the first part of this cleaning mode, when the probe 16 is in its down position, the whole upper outside portion of the probe 16 is washed and dryed in the cleaning chamber 44. At such time the flow of wash fluid W is directed from center ports 54 is being drawn past the upper portion of the probe 16, and both it and a flow of air, are discharged and exhausted, respectively, simultaneously through the opened lower ports 56 to waste. The air being drawn into the cleaning chamber 44, through its mouth 71, from the atmosphere, thereby preventing the exiting of the wash fluid W from the mouth of the cleaning chamber 44. As the probe 16 is retracted toward its up position, during the second part of the cleaning mode, initially only the lower ports 56 are open to discharge the flow of washing fluid W and, as previously described, to simultaneously draw air therethrough to prevent the washing fluid from exiting from the cleaning chamber 44. It is believed that the achievement of a virtually contaminant-free apparatus is attributed, in part, at least to the wash fluid W from the first means 58 forming, during the cleaning mode, an outwardly and laterally extending moving meniscus at the mouth 71 of the cleaning chamber 44 which extends a distance sufficient to encompass any contaminant at its mouth 71 deposited as a result of the probe 16 being retracted within internal passageway 42, which moving meniscus is maintained at the mouth 71 by the second means 68, which includes the lower ports 56, to which vacuum $V_L$ is applied, until the probe tip 30 has been withdrawn past the mouth 71. When the probe 16 is fully retracted to the up position, both series of upper and lower ports 52 and 56, respectively, remain open to continue to remove the washing fluid W. When, as previously described, the lower ports 56 are closed, the upper ports 52 which remain open, function solely to remove the continuing flow of washing fluid W. Also, as previously described, when the flow of washing fluid W from center ports 54 is subsequently terminated and the center ports 54 are opened to the vacuum $V_C$, while the upper ports 52 remain open, both series of center and upper ports 54 and 52, respectively, now remove any remaining wash liquid W and sample contaminants from the outside of the probe 16 and its passageway 42 and then dry them by drawing into the upper portion of the cleaning chamber 44, through its mouth 71, a flow of air from the atmosphere through both the opened ports 54 and 52. After a desired interval sufficient for such drying, both series of open ports 52 and 54 are closed. This cleaning mode is initiated very shortly after the sample is aspirated and while the sample is still fresh, so as to decrease the possibility of the sample, when it constitutes blood, coagulating on the tip 30, or any other portion of the probe 16, or in the passageway 42, or at the mouth 71 of the cleaning chamber 44, which makes subsequent removal more difficult. While the probe 16 is still in its retracted or up position, the sample is delivered to the associated cell analyzing and sorting system. Then its interior is flushed by introducing washing fluid therethrough under pressure and drawing the washing fluid through the lower and center ports 56 and 54, respectively, which are opened to vacuum $V_L$ and $V_C$, respectively, for such purpose. Then the same cleaning cycle or mode, described above, is repeated, except that all the sequence of steps are performed while the probe 16 remains in its retracted or up position, thereby cleaning and drying only the probe tip 30.

It should be noted that when mixing of the sample in its container 26 is desired, a mixing cycle is initiated prior to aspiration, which preferably includes aspiration of a small amount of sample into the probe, preferably 100 ul, then delivering or returning it back to the same well of the sample container 26, and repeating this procedure another two times. It should also be noted that there is an intersurface flow of washing fluid between or along the walls 43 of said cleaning chamber 44 and the outside or exterior wall of said probe 16 during the period of time the wash fluid is directed against the probe 16 and drawn past it by the vacuums $V_L$, $V_C$ and $V_U$.

The operative parameters of the preferred embodiment of the invention are as follows, dimensions being given in inches:

| PORT DIAMETERS | | |
| --- | --- | --- |
| Lower (56) | Center (54) | Upper (52) |
| .086 | .013 | .086 |

| CLEANING CHAMBER (44) | |
| --- | --- |
| Length | Diameter |
| 1.68 | .090 |

| Distance from Mouth (71) to Center of the Ports | | |
| --- | --- | --- |
| Lower (56) | Center (54) | Upper (52) |
| 0.100 | 0.860 | 1.460 |

| PROBE (16) | | |
| --- | --- | --- |
| Length | Outside Diameter | Inside Diameter |
| 8.07 | .062 ± .001 | .010 ± .001 |

The vacuum at the vacuum pump (not shown) is approximately ten PSI and the vacuum at the fittings 76, 66 and 82, is greater than five PSI and the wash fluid is pressurized to a similar, positive, value.

Accordingly, an improved microsample handling apparatus and method has been disclosed for cleaning, washing and drying a sample probe 16, particularly its exterior, which apparatus 10 is both simple, in design and operation, and compact and wherein sample contamination is virtually eliminated. In operation there is no relative lateral movement between the probe 16 and its cleaning station 18; also the probe 16, is contrained to vertical displacement. During the sampling and cleaning, the apparatus 10 is fixed in place laterally and is ideally suited for automatically processing a large number of open samples.

Many modifications and variations of the present invention are possible in light of the above teachings. For example, although a series of two, four, and two passageways are illustrated for the lower, center and upper side passageways 70, 60, and 78, respectively, there could be more for the upper and lower and less for the center. Also, the microsample handling apparatus 10 can be molded or machined or otherwise formed from plastic or other convenient material.

It should be understood that this invention is not limited to the specific details of construction and arrangement or method steps herein illustrated and or described and that changes and modifications may occur to one skilled in the art without departing from the spirit and scope of the invention.

What is claimed is:

1. A method of cleaning a fluid probe means, having a probe tip, within a cleaning chamber of a cleaning station, said cleaning chamber having a first, open end and a second end, and a plurality of cleaning ports, comprising:
    moving said probe means to be cleaned into said cleaning chamber, and
    externally:
        directing a flow of washing fluid against said probe means while said probe tip extends beyond the open end of said cleaning chamber,
        drawing said flow of washing fluid past said probe means, and
        drawing a flow of gas from the atmosphere past said probe tip when said probe tip is within said cleaning chamber.

2. A cleaning method according to claim 1, wherein said drawing of the flow of washing fluid past said probe means is in the direction toward said second end of said cleaning chamber.

3. A cleaning method according to claim 1, wherein said drawing of the flow of gas from the atmosphere is toward said second end of said cleaning chamber past said probe means.

4. A cleaning method according to claim 1, further including the step of discharging and exhausting the flow of washing fluid and gas, respectively, through the same cleaning ports.

5. A cleaning method according to claim 1, further including the steps of:
    forming an outwardly and laterally extending moving meniscus of wash fluid at said open end which meniscus extends a distance sufficient to encompass any contaminant at said open end deposited as a result of said probe being moved toward said cleaning chamber, and
    maintaining said meniscus at said open end of said cleaning chamber.

6. A microsample handling apparatus comprising:
    a probe means, having an exterior wall, for aspirating a sample; and
    a cleaning means including,
        a passageway within which said probe means is movable, and wherein said passageway includes walls which define a cleaning chamber having opposite ends, one end of which is open to the atmosphere and proximate to said sample,
        a first means, disposed between the ends of said cleaning chamber, for directing a washing fluid against said probe means during a cleaning mode, and
        a second and third means, disposed at the opposite ends of said cleaning chamber, for applying a vacuum to said cleaning chamber for
            removing said washing fluid, and
            drying said probe means and preventing the exiting of said wash fluid, by permitting a gas to flow into said cleaning chamber
        said probe means and said cleaning chamber so constructed and arranged for providing an intersurface flow of said washing fluid between the walls of said cleaning chamber and the exterior wall of said probe means along substantially the full length of that portion of the probe means which is positioned between the upper and lower ports of said cleaning chamber.

7. An apparatus according to claim 6, wherein said third means is disposed distally from said sample and removes said washing fluid when said probe means is in a retracted position wherein its probe tip is disposed between the ends of said cleaning chamber.

8. An apparatus according to claim 6, wherein said probe means having an opening at its lower end.

9. An apparatus according to claim 8, wherein said cleaning chamber has an upper closed end and wherein said third means is disposed at said upper end of said cleaning chamber for drying said probe means.

10. An apparatus according to claim 6, wherein said first means includes fourth means for applying a vacuum thereto for removing said washing fluid and drying said probe.

11. An apparatus according to claim 6, wherein said probe means is axially movable.

12. An apparatus according to claim 10, wherein said fourth means for applying a vacuum removes said wash fluid from the probe means and passageway and drys said passageway.

13. An apparatus according to claim 6, wherein said first means forms an outwardly and laterally extending moving meniscus of wash fluid at said open end which meniscus extends a distance sufficient to encompass any contaminant at said open end deposited as a result of said probe means being moved toward said cleaning chamber, and said second means is disposed at said open end and maintains said meniscus at said open end.

14. The cleaning method according to claim 1, wherein said flow of washing fluid is drawn past at least a portion of said probe means which remains within said cleaning chamber while said probe tip extends beyond the open end of said cleaning chamber.

15. The cleaning method according to claim 1, wherein said flow of gas from the atmosphere is drawn past said probe means when its probe tip extends beyond the open end of said cleaning chamber.

16. A microsample handling apparatus comprising:
a probe means for aspirating a sample; and
a cleaning means including,
  a passageway within which said probe means is movable, and wherein said passageway, has a cleaning chamber having opposite ends, one end of which is open to the atmosphere and proximate to said sample,
  a first means, disposed between the ends of said cleaning chamber, for directing a washing fluid against said probe means during a cleaning mode, and
  a second and third means, disposed at the opposite ends of said cleaning chamber, for applying a vacuum to said cleaning chamber for
    removing said washing fluid, and
    drying said probe means and preventing the exiting of said wash fluid, by permitting a gas to flow into said cleaning chamber,
  said cleaning chamber having a substantially uniform diameter between said second and third means.

17. A microsample handling apparatus comprising:
a probe means for aspirating a sample; and
a cleaning means including,
  a passageway within which said probe means is movable, and wherein said passageway has a cleaning chamber formed of a single chamber and having opposite ends, one end of which is open to the atmosphere and proximate to said sample,
  a first means, disposed between the ends of said cleaning chamber, for directing a washing fluid against said probe means during a cleaning mode, and
  a second and third means, disposed at the opposite ends of said cleaning chamber, for applying a vacuum to said cleaning chamber for
    removing said washing fluid, and
    drying said probe means and preventing the exiting of said wash fluid, by permitting a gas to flow into said cleaning chamber.

18. A method of cleaning a fluid probe means, having an exterior wall and a probe tip, within walls which define a cleaning chamber of a cleaning station, said cleaning chamber having a first, open end and a second end, and a plurality of cleaning ports, comprising:
moving said probe means to be cleaned into said cleaning chamber, and .
externally:
  directing a flow of washing fluid against said probe means and producing an intersurface flow of said washing fluid between the walls of said cleaning chamber and the exterior wall of said probe means along substantially the full length of that portion of the probe means which is positioned between the first, open, end and the second end of said cleaning chamber,
  drawing said flow of washing fluid past said probe means, and
  drawing a flow of gas from the atmosphere past said probe tip when said probe tip is within said cleaning chamber.

19. A cleaning method according to claim 1, wherein said directing of the flow of washing fluid against said probe means continues until said probe means tip is at least retracted within said cleaning chamber.

20. A method of cleaning a fluid probe means, having a probe tip, within a cleaning chamber of a cleaning station, said cleaning chamber having a first, open end and a second end, and a plurality of cleaning ports, comprising:
moving said probe means to be cleaned into said cleaning chamber, and
externally:
  directing a flow of washing fluid against said probe means,
  drawing said flow of washing fluid past said probe means and maintaining said flow of washing fluid around that portion of the probe means which enters the open end of said cleaning chamber, and
  drawing a flow of gas from the atmosphere past said probe tip when said probe tip is within said cleaning chamber.

* * * * *